United States Patent [19]

Kume et al.

[11] 4,287,059
[45] Sep. 1, 1981

[54] DIALYZER APPARATUS IN AN ARTIFICIAL KIDNEY SYSTEM

[75] Inventors: Tadashi Kume; Isamu Inoh, both of Tokyo, Japan

[73] Assignee: Honda Giken Kogyo Kabushiki Kaisha, Tokyo, Japan

[21] Appl. No.: 47,999

[22] Filed: Jun. 13, 1979

[30] Foreign Application Priority Data

Jun. 15, 1978 [JP] Japan ................................ 53-71528

[51] Int. Cl.³ ....................... B01D 13/00; B01D 19/00
[52] U.S. Cl. .................................... 210/188; 210/206; 210/321.3
[58] Field of Search ....... 210/321 B, 321 A, DIG. 23, 210/87, 188, 206; 128/214 B

[56] References Cited

U.S. PATENT DOCUMENTS

| 3,809,241 | 5/1974 | Alvine | 210/321 B |
|---|---|---|---|
| 3,946,731 | 3/1976 | Lichtenstein | 128/DIG. 3 |
| 4,028,253 | 6/1977 | Miller et al. | 210/321 B |
| 4,079,007 | 3/1978 | Hutchisson | 210/321 B |
| 4,141,835 | 2/1979 | Schäel et al. | 210/321 B |
| 4,141,836 | 2/1979 | Schäel | 210/321 B |
| 4,180,460 | 5/1979 | Calari | 210/321 B |

FOREIGN PATENT DOCUMENTS

| 1881611 | 3/1960 | Fed. Rep. of Germany | 210/321.3 |
|---|---|---|---|
| 2235928 | 2/1973 | Fed. Rep. of Germany | |
| 2259787 | 7/1973 | Fed. Rep. of Germany | |
| 2332445 | 1/1975 | Fed. Rep. of Germany | |
| 2550340 | 5/1977 | Fed. Rep. of Germany | |

OTHER PUBLICATIONS

"Med. Technik", 94th year, No. 2/74, pp. 33-36.

Primary Examiner—Charles N. Hart
Assistant Examiner—E. Rollins Cross
Attorney, Agent, or Firm—Haseltine & Lake

[57] ABSTRACT

A dialyzer apparatus in an artificial kidney system comprising a dialyzer main body having therein a blood flow passage and a dialyzing liquid flow passage separated by a dialyzing membrane. Integrally formed at the front surface of the main body is an air removal chamber which is in communication with the outlet of the blood flow passage and a liquid level adjusting chamber which is in communication with the air removal chamber. A pipe passage extends downwards from the air removal chamber for return of purified blood to the patient. The main body of the dialyzer is also integrally formed at its rear surface with a pair of further pipe passages which are respectively in communication with the inlet and outlet of the dialyzing liquid flow passage. A bottom cover member has a pair of medical liquid chambers integrally formed therewith and the bottom cover is mounted on and connected to the lower surface of the main body. The medical liquid chambers respectively communicate with the inlet and the outlet of the blood flow passage.

6 Claims, 5 Drawing Figures

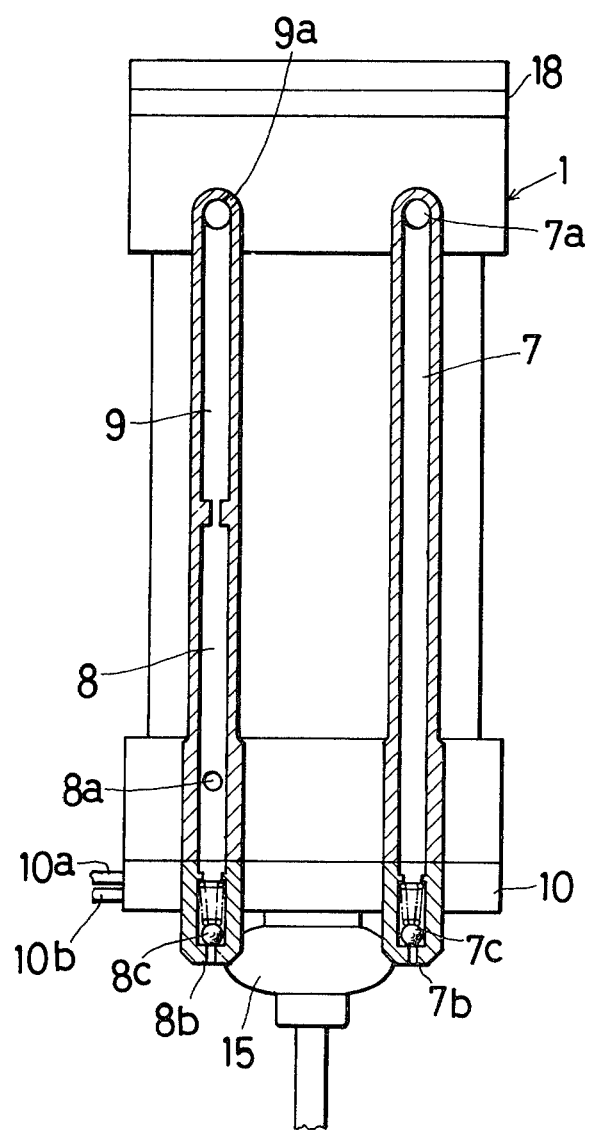

DIALYZER APPARATUS IN AN ARTIFICIAL KIDNEY SYSTEM

FIELD OF THE INVENTION

This invention relates to a dialyzer apparatus in an artificial kidney system.

PRIOR ART

It has been conventional in artificial kidney systems for the dialyzer apparatus to comprise a main body in which a blood flow passage and a dialyzing liquid flow passage are partitioned by a dialyzing membrane in an outer casing.

This conventional construction has the disadvantage that it must be connected to separately prepared respective parts through respective tubes mounted at its respective connection openings, so that not only is the apparatus troublesome in assembly but it also tends to become comparatively large-sized. Additionally, there is the danger that the tubes inadvertently may come off, and further the tubes are comparatively long and thereby a comparatively large amount of blood is required.

SUMMARY OF THE INVENTION

An object of this invention is to provide a dialyzer apparatus free from the above disadvantages.

The invention is characterized in that a dialyzer main body having therein a blood flow passage and a dialyzing liquid flow passage which are partitioned by a dialyzing membrane is formed integrally at its front surface with an air removal chamber which is in communication with an outlet side of the blood flow passage, a liquid level adjusting chamber which is in communication with the air removal chamber, and a pipe passage extending downwards from the air removal chamber, and is also formed integrally at its rear surface with a pair of pipe passages which are in communication with inlet and outlet sides, respectively, of the dialyzing liquid flow passage; and a bottom cover member having a pair of medical liquid chambers formed integrally therewith mounted on and connected to the bottom surface of the main body.

BRIEF DESCRIPTION OF THE FIGURES OF THE DRAWING

FIG. 4 is a sectional view taken along line IV—IV in FIG. 1.

DETAILED DESCRIPTION

Figure 1:
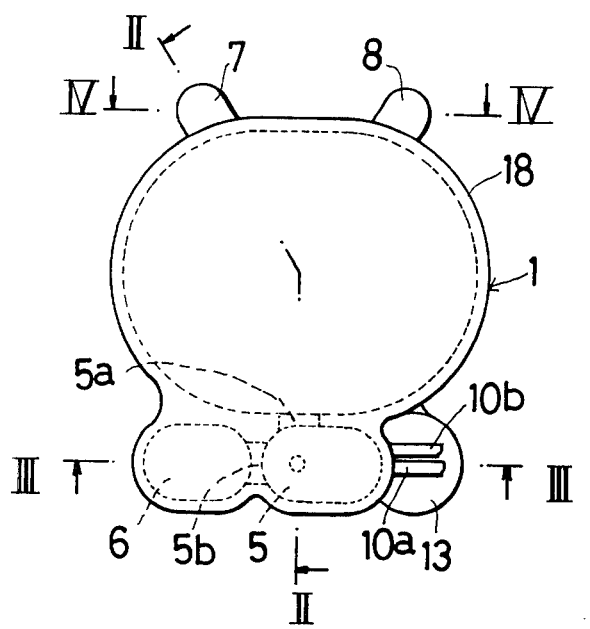
FIG. 1 is a top plan view of one embodiment according to this invention.
Figure 5:
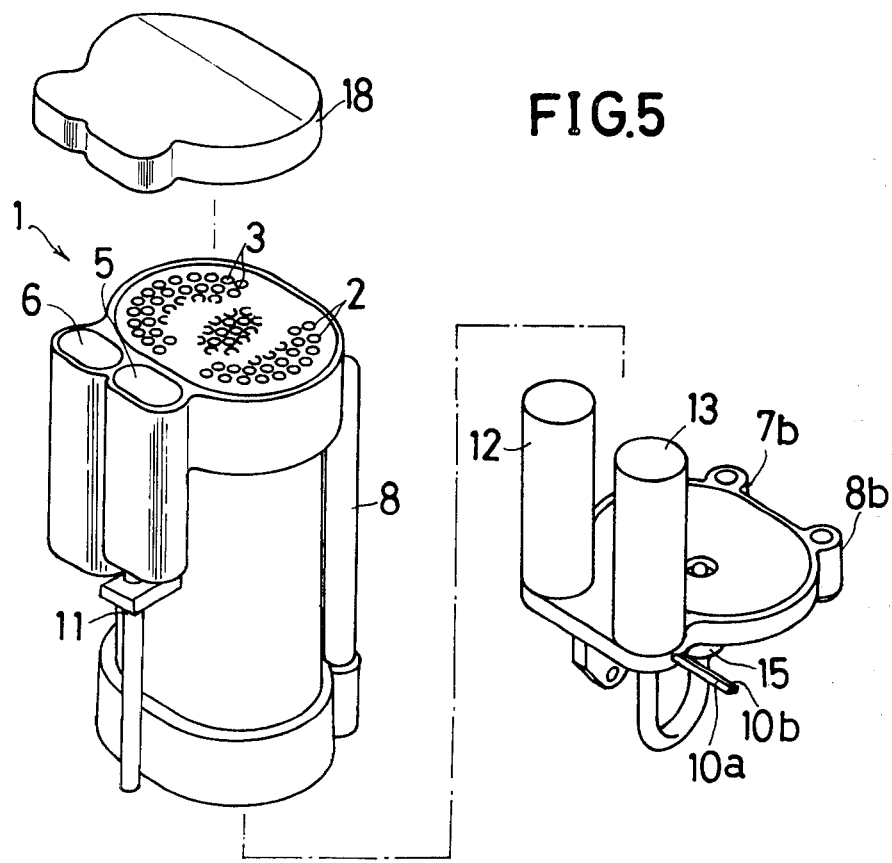
FIG. 5 is an exploded perspective view of the embodiment.
Figure 2:
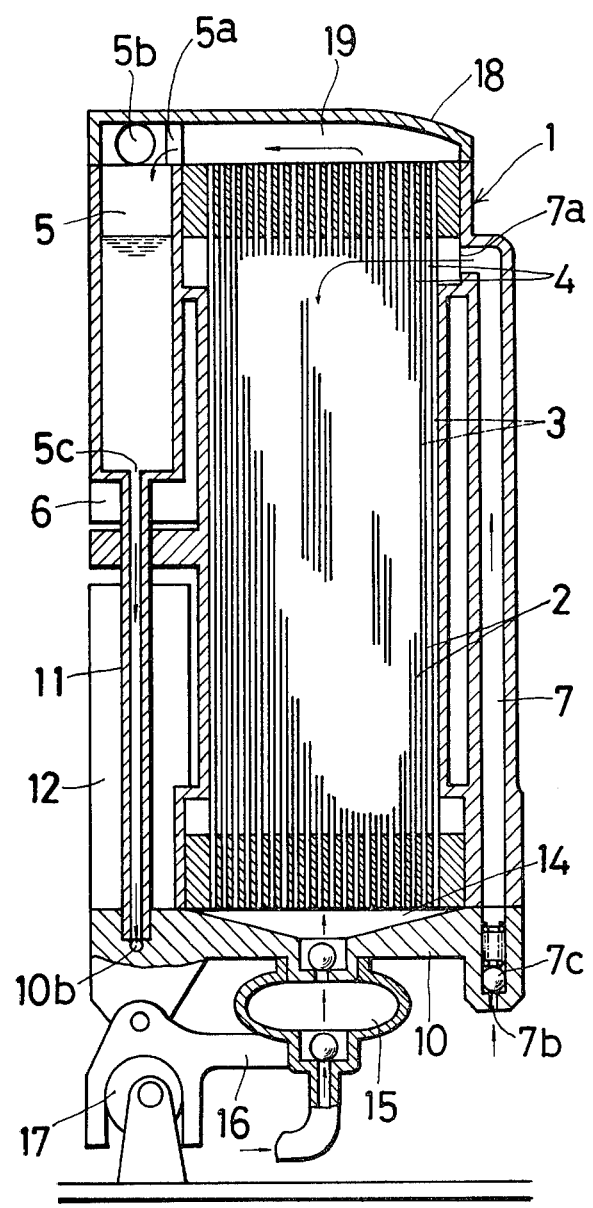
FIG. 2 is a sectional view taken along line II—II in FIG. 1.
Figure 3:
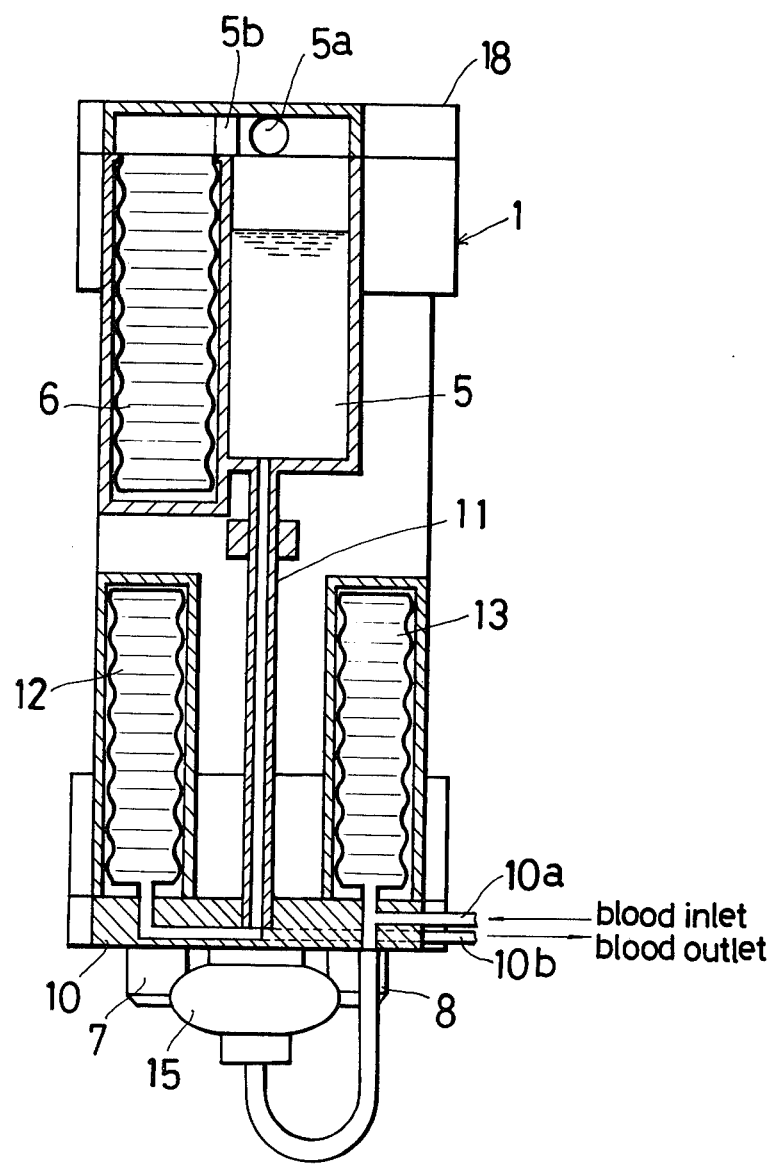
FIG. 3 is a sectional view taken along line III—III in FIG. 1.

Referring to the drawings, numeral 1 denotes a dialyzer main body of tubular form, and the body is provided therein with a blood flow passage 3 and a dialyzing liquid flow passage 4 which are partitioned by a dialyzing membrane 2. In greater detail, the dialyzing membrane 2 is composed of a large number of fine tubes extending vertically in the main body 1, and thereby the blood flow passage 3 is composed of a large number of passages inside the fine tubes while the dialyzing liquid flow passage 4 is composed of a large number of passages outside the fine tubes. This construction is not especially different from that of the conventional dialyzer.

According to this invention, an air removal chamber 5 and a liquid level adjusting chamber 6 are disposed adjacent one another at the front of the main body 1 and the chambers are integrally formed with the body. The air removal chamber 5 is in communication with an outlet side, that is, a top end of the blood flow passage 3 and the liquid level adjusting chamber 6 is in communication with the air removal chamber. At the front of the body is also a pipe passage 11 extending downwards from the air removal chamber 5 and formed integrally therewith. The air removal chamber 5 is in communication through an opening 5a with the outlet side of the blood flow passage 3 and is also in communication through an opening 5b with the liquid level adjusting chamber 6. Chamber 5 is also in communication through an opening 5c with the pipe passage 11.

Additionally, a pair of pipe passages 7, 8 which are in communication with respective inlet and outlet sides of the dialyzing liquid flow passage 4 are disposed adjacent one another at the rear of the main body 1 and are formed integrally therewith. The pipe passage 8 on the outlet side is extended upwards to form an air removal pipe passage 9. The pipe passage 7 is in communication, through an opening 7a at its upper end, with the inlet side, that is, the upper end of the dialyzing liquid flow passage 4, and the pipe passage 8 is in communication, through an opening 8a near the lower end thereof, with the outlet side, that is, the lower end of the passage 4, and the air removal pipe passage 9 is provided at its upper end with an air vent opening 9a. Furthermore, the pipe passages 7, 8 are formed at their lower end portions with respective connection openings 7b, 8b, provided with respective valves 7c, 8c which are arranged to be opened at the time of connection. The openings 7b, 8b are formed integrally with a bottom cover member 10 which will be described hereafter.

The bottom cover member 10 previously prepared separately from the main body 1 is mounted on the bottom surface of the dialyzer main body 1 and is fixedly connected thereto by melting the two together or the like. The member 10 has on the front, upper surface thereof a pair of adjacent medical liquid chambers 12, 13 formed integrally therewith. Additionally, the member 10 is formed at its upper surface with an inlet chamber 14 which is in communication with the inlet side, that is, the lower end of the blood flow passage 3. A blood pump 15 is mounted on the lower side of the cover member 10.

The pump 15 is connected to an electric motor (not illustrated), by a belt or the like, through a rocker arm 16 on its front side and a cam 17 which is in engagement with the rocker arm 16. Furthermore, the member 10 has a pair of upper and lower connection passages 10a, 10b projecting integrally therefrom, and the connection passage 10a is in communication with the medical liquid chamber 13 and the inlet side of the pump 15, and the connection passage 10b is in communication with the lower end of the pipe passage 11 and the medical liquid chamber 12.

In the illustrated embodiment, an upper cover member 18 is previously prepared separately from the main body 1, and the cover member 18 is mounted on the top surface of the dialyzer main body 1 and is connected hereto by melting the two together, or the like. The openings 5a, 5b are made in the lower surface of the cover member 18, and an outlet chamber 19 which is to be in communication with the outlet side of the blood flow passage 3 is also formed in the cover member 18. In general, all the constructional components, that is, the dialyzer main body 1, the bottom cover member 10 and the upper cover member 18 are made of synthetic resin.

The operation of the apparatus is as follows.

Blood is supplied from the connection passage 10a through the blood pump 15 into the blood flow passage 3 and flows therethrough upwards and thereafter is passed through the air removal chamber 5 and the pipe passage 11 and is discharged from the connection passage 10b. In the meanwhile, dialyzing liquid is supplied from the connection opening 7b through the pipe passage 7 into the dialyzing liquid flow passage 4 and flows therethrough downwards and thereafter passes from the opening 8a through the pipe passage 8 and is discharged from the connection opening 8b. During this circulation, the blood and the dialyzing liquid interact through the dialyzing membrane 2 so that the blood is purified.

Thus, according to this invention, the main body of the dialyzer is provided integrally on its front and rear sides respectively with a pair of chambers and a pair of pipe passages, and the main body is provided with a single pipe passage; additionally, the bottom cover member on the bottom surface of the body is integrally provided with a pair of chambers, so that the overall apparatus can be comparatively small-sized, and there is no danger that each connecting portion may separate inadvertently while additionally, each connecting portion can be greatly decreased in length, and consequently the use of a large amount of blood becomes unnecessary.

What is claimed is:

1. A dialyzer apparatus in an artificial kidney system comprising a dialyzer main body having therein a blood flow passage and a dialyzing liquid flow passage, a top cover member mounted on and connected to the upper surface of the dialyzer main body, a dialyzing membrane separating the blood flow passage and the dialyzing liquid flow passage, said blood flow passage and dialyzing liquid flow passage having respective inlets and outlets, said body having upper and lower surfaces and front and rear surfaces, said body being formed integrally at its front surface with (a) an air removal chamber which is in communication with the outlet of said blood flow passage, (b) a liquid level adjusting chamber which is in communication with the air removal chamber, and (c) a pipe passage extending downwards from the air removal chamber, said body being also formed integrally at its rear surface with a pair of further pipe passages which are in communication with the inlet and outlet respectively, of the dialyzing liquid flow passage, and a bottom cover member having a pair of chambers formed integrally therewith mounted on and connected to the lower surface of the main body, said bottom cover member including two connection passages constituting an inlet and outlet respectively for said blood flow passage, said inlet passage communicating with one of said chambers, and said outlet passage communicating with the other of said chambers.

2. A dialyzer apparatus as claimed in claim 1, wherein the dialyzer main body and the bottom cover member are made of synthetic resin.

3. A dailyzer apparatus as claimed in claim 1 wherein said top cover member is made of synthetic resin.

4. A dialyzer apparatus as claimed in claim 1 comprising a blood pump mounted on said bottom cover member and having an inlet connected to.

5. A dialyzer apparatus as claimed in claim 1 wherein said chambers extend within said main body.

6. A dialyzer apparatus as claimed in claim 1 comprising an air removal pipe passage in communication with the outlet of the dialyzing liquid flow passage.

* * * * *